United States Patent
Turpin, Jr.

(10) Patent No.: US 8,220,344 B2
(45) Date of Patent: Jul. 17, 2012

(54) METHOD FOR ESTIMATING PROPERTIES OF CONCRETE

(75) Inventor: Raymond C. Turpin, Jr., Atlanta, GA (US)

(73) Assignee: U.S. Concrete, Inc., Houston, TX (US)

(*) Notice: Subject to any disclaimer, the term of this patent is extended or adjusted under 35 U.S.C. 154(b) by 553 days.

(21) Appl. No.: 12/503,622

(22) Filed: Jul. 15, 2009

(65) Prior Publication Data

US 2011/0011161 A1    Jan. 20, 2011

(51) Int. Cl.
*G01N 33/00* (2006.01)

(52) U.S. Cl. .......................................... 73/866

(58) Field of Classification Search .................. 73/866
See application file for complete search history.

(56) References Cited

U.S. PATENT DOCUMENTS

| | | | | |
|---|---|---|---|---|
| 4,002,713 A * | 1/1977 | Duncan et al. | ............... | 264/234 |
| 4,018,617 A | 4/1977 | Nicholson | | |
| 4,052,220 A * | 10/1977 | Turpin, Jr. | ............... | 588/257 |
| 4,615,215 A * | 10/1986 | Sugimoto et al. | ............... | 73/866 |
| 5,520,730 A | 5/1996 | Barbour | | |
| 6,384,141 B2 * | 5/2002 | Hirata et al. | ............... | 525/187 |
| 6,451,105 B1 | 9/2002 | Turpin, Jr. | | |
| 6,468,344 B1 | 10/2002 | Liang et al. | | |
| 6,664,360 B2 * | 12/2003 | Shen | ............... | 528/75 |
| 6,712,900 B2 * | 3/2004 | Wombacher et al. | ............... | 106/823 |
| 6,858,074 B2 | 2/2005 | Anderson et al. | | |
| 2001/0013302 A1 | 8/2001 | Mathur et al. | | |
| 2002/0014187 A1 | 2/2002 | Greenwood et al. | | |
| 2002/0107310 A1 | 8/2002 | Shendy et al. | | |
| 2003/0030450 A1 | 2/2003 | Devine | | |
| 2003/0127026 A1 | 7/2003 | Anderson et al. | | |
| 2003/0181579 A1 | 9/2003 | Porsch et al. | | |
| 2003/0188591 A1 * | 10/2003 | Workman | ............... | 73/866 |
| 2004/0127606 A1 | 7/2004 | Goodwin | | |
| 2004/0149174 A1 | 8/2004 | Farrington et al. | | |
| 2004/0198873 A1 | 10/2004 | Bury et al. | | |
| 2005/0072339 A1 | 4/2005 | Jardine et al. | | |
| 2005/0139129 A1 | 6/2005 | Daczko et al. | | |
| 2005/0274294 A1 | 12/2005 | Brower et al. | | |
| 2006/0030643 A1 | 2/2006 | Bury et al. | | |
| 2006/0243169 A1 | 11/2006 | Mak et al. | | |
| 2006/0281835 A1 | 12/2006 | Ong | | |

(Continued)

FOREIGN PATENT DOCUMENTS

DE            32 37 090 A1    4/1984

(Continued)

OTHER PUBLICATIONS

Dale P. Bentz, Kenneth A. Snyder and Paul E. Stutzman; Microstructural Modelling of Self-Dessiccation During Hydration, Conference Proceedings of an International Research Seminar entitled "Self-Desiccation and its Importance in Concrete Technology"; Jun. 10, 1997; Published by the Lund Institute of Technology, Division of Building Materials; Lund, Sweden.

(Continued)

*Primary Examiner* — Hezron E Williams
*Assistant Examiner* — Nathaniel Kolb
(74) *Attorney, Agent, or Firm* — Alston & Bird LLP

(57) ABSTRACT

Provided are procedures for estimating the amount of water vapor emissions as well as other properties, such as slump and volume yield, of a concrete or cementitious mix used in producing a concrete.

9 Claims, 1 Drawing Sheet

U.S. PATENT DOCUMENTS

| | | |
|---|---|---|
| 2006/0281836 A1 | 12/2006 | Kerns et al. |
| 2007/0125273 A1 | 6/2007 | Pinto |
| 2007/0256605 A1 | 11/2007 | Aldykiewicz, Jr. et al. |
| 2007/0266905 A1 | 11/2007 | Amey et al. |
| 2008/0058446 A1 | 3/2008 | Guevara et al. |
| 2008/0087199 A1 | 4/2008 | Gartner |
| 2008/0156225 A1 | 7/2008 | Bury |
| 2008/0171813 A1 | 7/2008 | Sprouts et al. |
| 2008/0178769 A1 | 7/2008 | Goodwin et al. |
| 2008/0227891 A1 | 9/2008 | Jarvie et al. |
| 2008/0275149 A1 | 11/2008 | Ladely et al. |
| 2009/0025613 A1* | 1/2009 | Testut et al. .......... 106/695 |

FOREIGN PATENT DOCUMENTS

| | | | |
|---|---|---|---|
| EP | 0 744 387 A1 | 11/1996 | |
| EP | 1 148 329 A1 | 10/2001 | |
| EP | 1 900 705 A1 | 3/2008 | |
| EP | 1 903 014 A1 | 3/2008 | |
| EP | 1 958 926 A1 | 8/2008 | |
| FR | 2 921 358 A1 | 3/2009 | |
| JP | 2001-289766 A | 10/2001 | |
| JP | 2008 254963 A | 10/2008 | |

OTHER PUBLICATIONS

Rougeau, P. et al., *Ultra High Performance Concrete With Ultrafine Particles Other Than Silica Fume*, Proceedings of the International Symposium on Ultra High Performance Concrete, Sep. 13, 2004, pp. 213-225.

International Search Report and Written Opinion for Application No. PCT/US2010/042109 dated Apr. 15, 2011.

Vejmelkova, E. et al., *High Performance Concrete Containing Lower Slag Amount: A Complex View of Mechanical and Durability Properties*, Construction and Building Materials, vol. 23, (2009), pp. 2237-2245.

Partial Search Report for International Application No. PCT/US2010/042056, dated Oct. 18, 2010.

Partial Search Report for International Application No. PCT/US2010/042109, dated Oct. 21, 2010.

* cited by examiner

METHOD FOR ESTIMATING PROPERTIES OF CONCRETE

FIELD OF INVENTION

Various embodiments of the present invention relate to cementitious compositions used in preparing a concrete having an attenuated rate of water vapor emissions after hardening. Various embodiments of the invention also relate to methods of preparing and using the cementitious compositions of the invention. Methods for estimating the amount of water vapor emissions that can be expected to occur after hardening of a cementitious mix as well as other associated properties of concrete are also provided, according to certain embodiments.

BACKGROUND OF THE INVENTION

Concrete generally refers to a mixture of natural and/or artificial aggregates, such as, for example, sand and either a gravel or a crushed stone, which is held together by a binder of cementitious paste to form a highly durable building material. The paste is typically made up of a hydraulic cement, such as Portland cement, and water and may also contain one or more chemical admixtures as well as supplementary cementing materials, such as, for example, fly ash or ground granulated blast furnace slag cement.

Early cements were based on calcined lime, which is produced by exposing limestone at an elevated temperature, for example, a temperature well in excess of 800° C., in the presence of an oxygen-containing atmosphere to form quicklime according the reaction in equation (1).

$$CaCO_3 \rightarrow CaO + CO_2(g) \quad (1)$$

Hydraulic limes are derived from calcined limes that have some amount of clay. The clay provides silicon and aluminum that react with the calcium from the limestone to produce cements having complex compounds that hydrate. These compositions even have the ability to harden underwater. Portland cement eventually evolved from these materials.

Most construction cements today are hydraulic, and most of these are based on Portland cement. Hydraulic cements set and harden after being combined with water, as a result of chemical reactions induced by the water, and demonstrate an improved strength and stability even under water after hardening.

Setting and hardening of hydraulic cements is caused by hydration reactions that occur between the compounds that make up the cement and water, which result in the formation of hydrates or hydrate phases. The cementitious composition begins to progressively stiffen leading to the onset of setting, where additional consolidation of the hydration reactants occurs. Hardening follows setting, which is characterized by a steady growth in the compressive strength of the material over a period that can range from a few days in the case of "ultra-rapid-hardening" cements to several years in the case of ordinary cements.

Portland cement consists of five major compounds as well as some additional minor compounds. The major compounds are tricalcium silicate, $3CaO.SiO_2$; dicalcium silicate, $2CaO.SiO_2$; tricalcium aluminate, $3CaO.Al_2O_3$; tetracalcium aluminoferrite, $4CaO.Al_2O_3.Fe_2O_3$; and gypsum, $CaSO_4.2H_2O$. The hydration of tricalcium silicate is represented by the reaction according to equation (2).

$$2(3CaO.SiO_2) + 11H_2O \rightarrow 3CaO.2SiO_2.8H_2O + 3Ca(OH)_2 \quad (2)$$

Upon the addition of water, the reaction rapidly progresses to release calcium and hydroxide ions. Once the water solution becomes saturated, the calcium hydroxide begins to precipitate forming a crystalline structure. Calcium silicate hydrate is also simultaneously formed. As the calcium hydroxide precipitates from solution, the tricalcium silicate continues to react to form calcium and hydroxide ions. The reaction is somewhat exothermic involving the evolution of heat as the reaction progresses.

The formation of calcium hydroxide and calcium silicate hydrate provides "seeds" around which calcium silicate hydrate may continue to form. At a certain point, the rate of reaction finally becomes controlled by the rate of diffusion of water molecules through the layer of calcium silicate hydrate that surrounds the unreacted tricalcium silicate, which progressively becomes slower as the layer of calcium silicate hydrate grows larger.

Dicalcium silicate is hydrated to form the same products as tricalcium silicate according to the reaction in equation (3).

$$2(2CaO.SiO_2) + 9H_2O \rightarrow 3CaO.2SiO_2.8H_2O + Ca(OH)_2 \quad (3)$$

However, the hydration of dicalcium silicate occurs much more slowly and is mildly exothermic in comparison to that for tricalcium silicate.

The reactions of the other major components of Portland cement are more complex and beyond the scope of the background discussion given here. However, the hydration of cement experiences five distinct phases. Phase I is characterized by rapid hydrolysis of the cement compounds and can result in a temperature increase of several degrees over a period of on the order of 15 minutes. The evolution of heat begins to dramatically slow in phase II, the dormancy period, which can last from one to three hours. In phases III and IV, the concrete begins to harden and the evolution of heat begins to increase due primarily to the continued hydration of tricalcium silicate. These phases can encompass a period of up to approximately 32 to 36 hours. Stage V marks a period of continued hydration, but at much lower rates, and continues as long as unreacted water and unhydrated silicates remain and can come in contact with one another. Stage V typically continues on the order of days, if not longer.

More commonly, modern-day cements are formulations of hydraulic cement blends. For example, a hydraulic cement, such as, for example, Portland cement, can comprise up to 75% of ground granulated blast furnace slag that results in a reduction in early strength but provides increased sulfate resistance and diminished heat evolution during the stiffening and hardening stages of the concrete.

Blended hydraulic cements can comprise one or more pozzolan materials, which are siliceous or aluminosiliceous materials that demonstrate cementitious properties in the presence of calcium hydroxide. The silicates and even aluminates of a pozzolan reacting with the calcium hydroxide of a cement form secondary cementitious phases (e.g., calcium silicate hydrates having a lower calcium to silicon ratio), which demonstrate gradual strengthening properties that usually begin to be realized after 7 days of curing.

A blended hydraulic cement may comprise up to 40% or more fly ash, which reduces the amount of water that must be blended with the cementitious composition allowing for an improvement in early strength as the concrete cures. Other examples of pozzolans that can be used in hydraulic cement blends include a highly reactive pozzolan, such as, for example silica fume and metakaolin, which further increases the rate at which the concrete gains strength resulting in a higher strength concrete. Current practice permits up to 40 percent or higher reduction in the amount of hydraulic cement used in the concrete mix when replaced with a combination of pozzolans that do not significantly reduce the final compressive strength or other performance characteristics of the resulting concrete.

The cementitious materials in concrete require water, typically known as chemical water or hydration water, to chemically evolve into a hard, crystalline binder. For example, Portland cements generally require up to about 40% of their weight as water in order to promote complete hydration and chemical reaction.

Excess water has conventionally been added to make concrete more plastic allowing it to flow into place. This excess water is known as water of convenience. A small amount of the water does escape as a result of solids settling during the plastic phase, evaporation at the atmospheric interface, and absorption into accepting interface materials. However, most of the water of convenience remains in the concrete during and immediately following hardening. The water of convenience can then escape into the atmosphere following the hardening of the concrete. The water of convenience may represent up to about 70% of the total water in the concrete.

The concrete construction and floor-covering industries may incur both construction delays and remedial costs as a result of water vapor emissions and water intrusion from concrete. For example, adhesives and coatings used in the construction of concrete floors are relatively incompatible with moisture that develops at the concrete surface. Moisture may also create an environment for promoting the growth of mold.

Water tightness in concrete structures is a measure of the ability of the hardened concrete to resist the passage of water. Water vapor emission is proportional to the state of relative dryness of the body of the concrete structure. Once isolated from external sources of water, water vapor emissions are derived from the amount of water that is used in excess of that needed to harden the cementitious materials, i.e., the water of convenience. Depending upon the atmospheric temperature and humidity at the surface and the thickness of the concrete, the elimination of excess water through water vapor emissions can take on the order of many months to reach a level that is compatible with the application of a coating or an adhesive.

Installation of an impermeable barrier on the surface of the concrete prior to reaching an acceptable level of dryness may result in moisture accumulation, adhesive failure, and a consequential failure of the barrier due to delamination. Premature application of coatings and adhesives increases the risk of failure, while the delay caused by waiting for the concrete to reach an acceptable level of dryness often results in unacceptable construction delays.

The floor covering industry has determined, depending on the type of adhesive or coating used, that a maximum water vapor emission rate of from 3 to 5 pounds of water vapor per 1,000 square feet per 24 hour period is representative of a state of slab dryness necessary before adhesive may be applied to the concrete floor.

There remains a need in the art for cementitious compositions that reduce the amount of time needed to reach a desired water vapor emission rate in concrete floors enabling a more timely application of coatings and adhesives.

It is known in the art that certain polymers classified as superplasticizers may be included in cement in order to reduce the amount of water of convenience needed to allow the cementitious mix to more readily flow into place. Certainly, a reduction in the amount of excess water remaining after the concrete hardens should lead to a reduction in the amount of time necessary to reach a desired water vapor emissions rate. However, the use of superplasticizers alone does not address other effects that influence the rate of water vapor emission from the hardened concrete.

There remains a need in the art for cementitious compositions that further reduce the amount of time necessary to reach a desired water vapor emission rate in concrete floors beyond that which is achieved through reduction in the amount of water required through the use of a superplasticizer additive.

BRIEF SUMMARY OF THE INVENTION

Various embodiments of the invention relate to cementitious compositions that result in a concrete having a reduced amount of time needed to achieve a desired water vapor emission rate. While not intending to be bound by theory, certain embodiments of cementitious compositions offer the improvement of providing a hardened concrete that allows for the application of coatings and adhesives sooner than concretes produced by cementitious compositions known in the art.

Certain embodiments of the invention provide an inventive analytical procedure for quickly estimating various properties of a concrete. The inventive can be preferred, in certain embodiments, because of its use of smaller quantities of mortar ingredients and a reduced sample size over the size of conventional concrete samples.

One of the various aspects of the invention provides methods for estimating a property of a concrete. In an embodiment of the invention, a method for estimating a property of a concrete comprising the steps of preparing a mortar mixture that is representative of a cementitious mix used to prepare the concrete; casting the mortar mixture into a sample; equilibrating the sample to a selected set of conditions; calculating a daily weight loss of the sample; and estimating the property of the concrete using an established correlation based on the daily weight loss. In certain embodiments, the property can be any of a water vapor emission, an internal relative humidity, a required water content, and a water to cementitious ratio.

In certain embodiments of the invention, the method for estimating a property of a concrete additionally comprises the step of curing the sample prior to the equilibrating step. In an embodiment of the invention, the step for curing the sample may comprise the steps of not sealing the sample for a predetermined period of time to initially facilitate water and any other vapor loss, subsequently sealing the sample, and then curing the sample for a period of time.

In a preferred embodiment of the invention, the mortar mixture contains all of the compounds of the cementitious mix used to prepare a concrete except that the mortar mixture will not contain any aggregate, preferably, any coarse aggregate. More preferably, the compounds of the mortar mixture will be compounded and proportioned substantially the same as the compounds of the cementitious mix.

In certain embodiments of the invention the step of preparing the mortar mixture is a procedure comprising the steps of combining a sufficient amount of water with an admix to form a paste mixture; adding a sand to the paste mixture to form a mortar mixture; mixing the mortar mixture; and continuing to add any additional water as the mortar mixture continues to be mixed to achieve a target workability.

In a preferred embodiment of the invention, the sample used in the procedure for estimating a property of a concrete has a surface to volume ratio of from about 0.6 $in^{-1}$ to about 0.8 $in^{-1}$. In another preferred embodiment of the invention, the sample has a depth that is about 1⅜ inches.

In an embodiment of the invention, a method is provided for estimating a slump of a cementitious mix comprising the steps of portioning a mortar mixture that is representative of a cementitious mix into two layers in an ASTM C128 cone; rodding each layer of the mortar mixture; leveling the surface of the mortar mixture; lifting the cone free of the mortar; determining a slump of the mortar mixture in a number of increments of a predefined length; and estimating the slump of the concrete mixture by dividing the number of increments by a conversion factor. In certain preferred embodiments of the invention, the predefined length of the increment in the method for estimating the slump is about 1/16 inch. In certain preferred embodiments of the invention, the conversion factor of the method for estimating slump is about 4.

In yet another embodiment of the invention, a method is provided for estimating a volume yield of cementitious mix that includes the steps of portioning a mortar mixture that is representative of a cementitious mix into two layers in an ASTM C185 volumetric cylinder; rodding each layer of the mortar mixture; consolidating each layer of the mortar mixture; leveling the surface of the mortar mixture; and estimating the volume yield by dividing the weight of components used to prepare the mortar mixture by the weight of the mortar mixture in the volumetric cylinder and multiplying by a volume the mortar mixture occupies in the volumetric cylinder.

BRIEF DESCRIPTION OF THE SEVERAL VIEWS OF THE DRAWINGS

Figure 1:
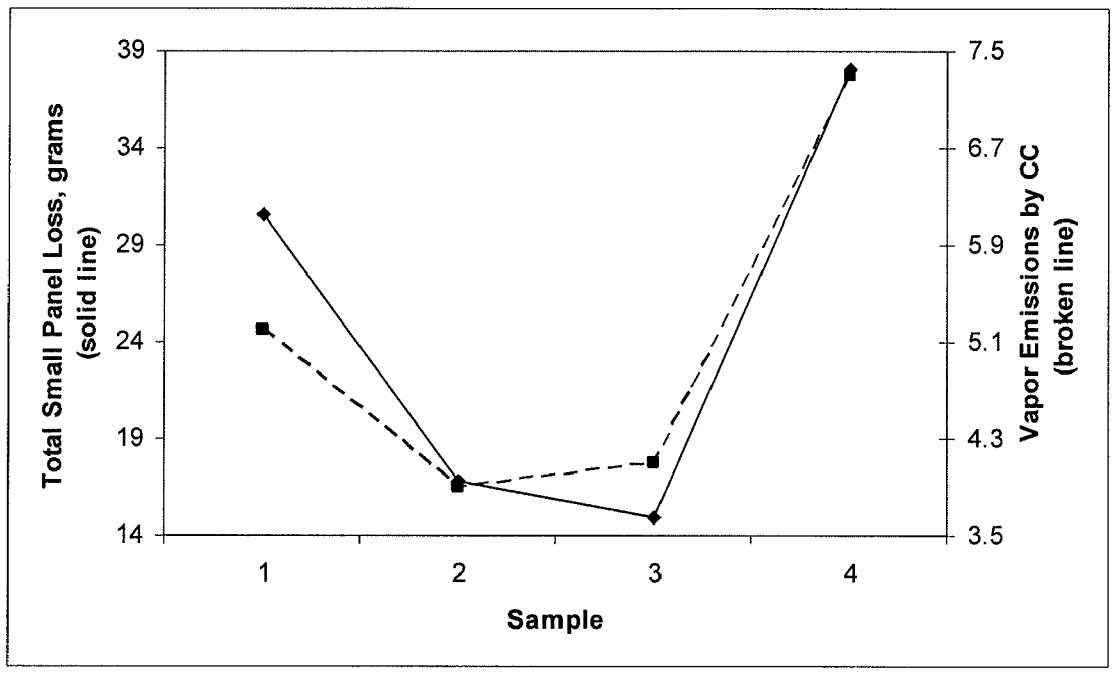
Figure 2:
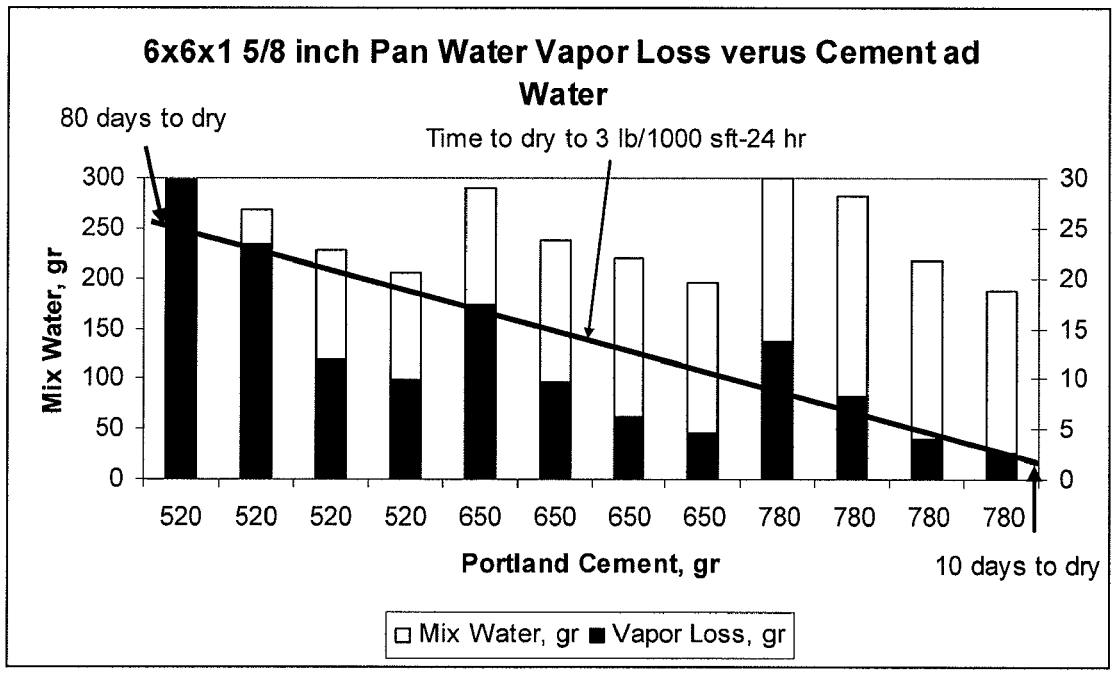

Having thus described the invention in general terms, reference will now be made to the accompanying drawings, which are not necessarily drawn to scale, and wherein:

FIG. 1 is a graphical illustration of the total small panel water vapor loss of a mortar against the corresponding water vapor loss by 2×2 foot panels of an associated concrete; and FIG. 2 is a graphical illustration of the water loss from the mortar pans versus the water vapor emissions measured from the concrete panels.

DETAILED DESCRIPTION OF THE INVENTION

The present invention now will be described more fully hereinafter with reference to the accompanying drawings, in which some, but not all embodiments of the inventions are shown. Preferred embodiments of the invention may be described, but this invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments of the invention are not to be interpreted in any way as limiting the various inventions described herein.

Although specific terms are employed herein, they are used in a generic and descriptive sense only and not for purposes of limitation. All terms, including technical and scientific terms, as used herein, have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise.

As used in the specification and in the appended claims, the singular forms "a", "an", and "the" include plural referents unless the context clearly indicates otherwise. For example, reference to "a concrete" includes a plurality of such concretes.

As used herein, "wt %" or "weight percent" or "percent by weight," unless specifically stated to the contrary, means a weight percentage of the component based on the total weight of the composition or article in which the component is included.

The term "attenuated water vapor emission," as used herein, means a cementitious composition that ultimately provides a cementitious mix that produces a hardened concrete that shows a reduction in the amount of time needed to achieve a desired water vapor emissions rate. In an embodiment of the invention, the desired water vapor emissions rate, for example, is 3 lb/1000 ft$^2$·24 hr. In certain embodiments of the invention, the attenuated water vapor emission may be measured based on the number of days required to achieve a desired internal relative humidity, for example, a 75% relative humidity.

The term "concrete structure," as used herein, is intended to be broadly defined to refer to any structure which is composed in at least significant part of concrete which has cured and hardened. A concrete structure includes, but is not limited to, a bridge, a roadway, a parking lot, a sidewalk, a curb, a parking garage, a floor, a patio slab, a support column, a pier, a marine structure, a piling, a conduit and any other paved surface whether located inside or outside.

As used herein, a "cement replacement" is a compound that partially substitutes for a compound that functions as the primary cement compound, such as, for example, a hydraulic cement, in a cementitious composition. Without intending to be bound by theory, the cement replacement itself may have binding properties similar to a cement. As such, any compound that can be chemically reacted or hydrolyzed by water to ultimately form other compounds that promote the hardening of a cement may, in certain embodiments, be a cement replacement. In some embodiments of the invention, the cement replacement may demonstrate cementitious properties because of their mere presence with another component of cement in the cementitious composition. A pozzolan is a non-limiting example of cement replacement that demonstrates cementitious properties when in the presence of another component of cement in the cementitious composition.

In certain embodiments of the invention, a cement replacement may be chosen to impart additional properties to the cement. In a non-limiting example, calcium carbonate may not only function as a cement replacement, but may also act as any one of a filler, a densifier, an accelerator of hydration, and any combination thereof. The compositions of the invention, in certain embodiments, may include these types of compounds as well.

As used herein, the term "cementitious composition" refers to a composition that includes a cement material and, optionally, any of a pozzolan, one or more fillers, adjuvants, additives, dispersants, and other aggregates and/or materials that, typically upon being combined with water, form a slurry that hardens to a concrete upon curing. Cement materials include, but are not limited to, hydraulic cement, gypsum, gypsum compositions, lime and the like.

As used herein, the term "cementitious mix" refers to the final mixture that comprises the compounds intended to be part of the formulation used to pour or cast a concrete. In a non-limiting example, the cementitious mix, in certain embodiments, comprises a cementitious composition and the desired amount of water.

As used herein, the term "fine calcium carbonate" means a calcium carbonate having a particle size of less than about 200 microns, less than about 150 microns, less than about 100 microns, and, preferably, less than about 75 microns. In certain embodiments of the invention, the fine calcium carbonate is introduced as part of a mixture that includes other compounds, such as, for example, alkaline earth and alkali metal carbonates. Of course, another source of fine calcium carbonate is limestone, for example, the crushed limestone marketed under the tradename of limestone fines available form Omya, Inc. (Alpharetta, Ga.). Limestone fines are generally understood to be small particulates of limestone, typically less than 65 mesh, though not intended to be limiting, generated when limestone is crushed or pulverized. In an exemplary embodiment of the invention, the fine calcium carbonate has a particle size of less than about 75 microns and is filtered from a ground mixture comprising calcium carbonate by using a standard sieve size having 75 micron openings or a varying plurality of openings of +/−75 microns.

The term "pozzolan," as used herein, refers to a siliceous or siliceous and aluminous material that, by itself, possesses substantially little or no cementitious value, but when, in particular, in a finely divided form and in the presence of water, chemically reacts with calcium hydroxide to form compounds possessing cementitious properties. Non-limiting examples of pozzolans include fly ash, silica fume, micronized silica, volcanic ashes, calcined clay, and metakaolin.

As used herein, the term "highly reactive pozzolan" are pozzolans that readily react with free lime to form a siliceous binder. Non-limiting examples of highly reactive pozzolans include silica fume and metakaolin.

The term "slump," as used herein when referring to a cementitious mix, means the amount of subsidence of a cementitious composition. Conventionally, slump has been measured by the ASTM C143 (2008 is the most recent specification) standard test procedure, which measures the amount of subsidence of a cementitious composition after removing a supporting cone, as specified in the test procedure.

The term "superplasticizer," as used herein, is defined as a water reducer, in particular, a high-range water reducer, or an additive that reduces the amount of water needed in a cementitious mix while still maintaining the workability, fluidity, and/or plasticity of the cementitious mix. Superplasticizers may include, but are not limited to formaldehyde condensates of at least one compound selected from the group consisting of methylolation and sulfonation products of each of naphthalene, melamine, phenol, urea, and aniline, examples of which include metal naphthalenesulfonate-formaldehyde condensates, metal melaminesulfonate-formaldehyde condensates, phenolsulfonic acid-formaldehyde condensate, and phenol-sulfanilic acid-formaldehyde co-condensates. Superplasticizers may also include the polymers and copolymers obtained by polymerizing at least one monomer selected from the group consisting of unsaturated monocarboxylic acids and derivatives thereof, and unsaturated dicarboxylic acids and derivatives thereof. Indeed, in preferred embodiments of the invention, the superplasticizer comprises a polycarboxylate superplasticizer.

The term "polycarboxylate superplasticizer" encompasses a homopolymer, a copolymer, and any combination thereof comprising a polycarboxylic to which other functional groups may be bonded. Preferably these other functional groups are capable of attaching to cement particles and other functional groups for dispersing the attached cement particle within an aqueous environment. Specifically, polycarboxylate superplasticizers are polymers with a carbon backbone having pendant side chains with the characteristic that at least a portion of the side chains are attached to the carbon backbone through a carboxyl group or an ether group. An exemplary polycarboxylate superplasticizer is given by Formula (I).

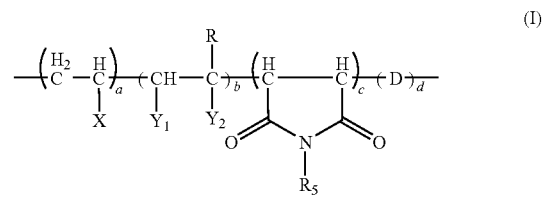

(I)

According to Formula (I):

D=a component selected from the group consisting of the structure according to Formula II, the structure according to Formula III, and combinations thereof.

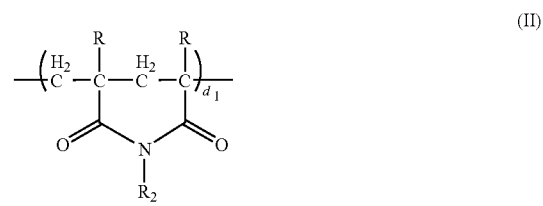

(II)

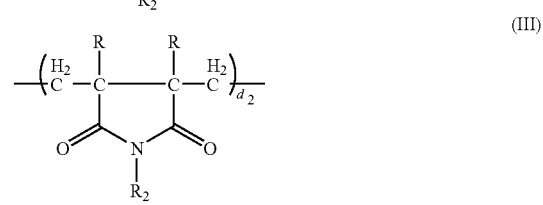

(III)

Additionally, according to Formulas (I), (II), and (III):

$X$=H, $CH_3$, $C_2$ to $C_6$ alkyl, phenyl, substituted phenyl;

$Y_1$=H, —COOM;

R=H, $CH_3$;

$Y_2$=H, —$SO_3M$, —$PO_3M$, —COOM, —$OR_3$, —$COOR_3$, —$CH_2OR_3$, —$CONHR_3$, —$CONHC(CH_3)_2$, $CH_2SO_3M$, —$COO(CHR_4)_nOH$ where n=2 to 6;

$R_1$, $R_2$, $R_3$, $R_5$ are each independently —$(CH_2CHRO)_mR_4$ random copolymer of oxyethylene units and oxypropylene units where m=10 to 500 and wherein the amount of oxyethylene in the random copolymer is form about 60% to about 100% and the amount of oxypropylene in the random copolymer is from about 0% to about 40%;

$R_4$=H, methyl, $C_2$ to $C_6$ alkyl;

M=alkali metal, alkaline earth metal, ammonia, amine, methyl, $C_2$ to $C_6$ alkyl;

a=0-0.8;

b=0.2-1.0;

c=0-0.5; and d=0-0.5.

a, b, c, d, $d_1$, and $d_2$ represent the mole fraction of each unit and the sum of a, b, c, and d is 1.0. The sum of $d_1$ and $d_2$ must be equal to d.

The term "water to cementitious ratio" is defined as the ratio of the mass of the water to the mass of the cementitious materials immediately present in the cementitious mix formed upon mixing a cementitious composition with the desired amount of water. Generally, when the cementitious composition also comprises a pozzolan, the mass of the pozzolan will be added to the mass of the cement in determining the water to cementitious ratio.

The terms "water vapor emission rate" and "water vapor emission(s)," as used interchangeably herein, refers to amount of water emitted from a 1,000 square foot surface area of concrete over a 24 hour period. The water vapor emission rate, in an embodiment of the invention, may be measured by the test described in ASTM F1869 (2004) entitled the "Standard Test Method for Measuring Moisture Vapor Emission Rate of Concrete Sub-Floor Using Anhydrous Calcium Chloride." ASTM F1869 measures the vapor emission rate by placing an airtight dome containing a specified weight of calcium chloride over the hardened concrete for a defined period of time.

As used herein, the term "workability" refers to the consistency and feel of a cementitious mixture or a mortar mixture. The requisite workability can vary based on the use of the cementitious and/or the mortar mixture. For example, depending on the application, the viscosity of the mixture may vary—e.g., a higher viscosity for applications where rapid flowability is not desired or a lower viscosity where rapid flowability is required, such as when performs are used. Of course, as understood in the art, other physical property parameters may also affect the workability of the mixture.

In another embodiment of the invention, the internal concrete moisture content may be determined using the procedure developed by the ASTM committee F.06, also known as the F2170 (2002) standard entitled "In-Situ Testing of Concrete Relative Humidity," which is commonly used in Europe. The F-2170-02 test procedure involves drilling ⅝ inch diameter holes to a depth equal to 40% of the thickness of the concrete slab. The hole is partially lined with a plastic sleeve that is capped at the entrance of the hole. The apparatus is allowed to acclimate to an equilibrium level for 72 hours prior to inserting a probe for measuring the internal relative humidity. The floor covering industry requires the internal relative humidity reading not to exceed 75% prior to application of a flooring adhesive.

In yet other embodiments of the invention, the water vapor emission rate is determined by a process or procedure provided, according to certain embodiments of the invention, for more quickly evaluating the potential water vapor emissions from concrete. The process or procedure, otherwise known herein as the "mortar method," comprises a procedure for preparing a representative mortar sample having a water to cementitious ratio that is consistent with that of the concrete to be proportioned. The prepared sample mixture, in an exemplary embodiment, is cast into a small mold having a preferred surface to volume ratio of about 0.67 in$^{-1}$ (6 inch×6 inch panels having a volume of about 54 cubic inches) to simulate the drying experienced by concrete that is exposed to the atmosphere at only one surface. The mortar is cast to a depth, which preferably approximates the depth of concrete that is immediately reactive to atmospheric temperature and moisture gradients. In certain embodiments of the invention, the mortar is cast to a depth of about 1½ inches. The cast samples of mortar are cured and periodically weighed at measured intervals in order to determine the amount of daily water loss. The water vapor loss is used to estimate the drying rate or some other property of a hardened concrete based upon a correlation. Various methods of estimating a water vapor emission rate or an internal relative humidity of a concrete using this procedure are further disclosed herein.

An aspect of various embodiments of the invention described herein relates to a cementitious composition, specifically to a cementitious composition resulting in a concrete having a reduced or an attenuated rate of water vapor emissions after hardening. The cementitious compositions preferably are formulated to include at least one superplasticizer. More preferably, the at least one superplasticizer comprises a polycarboxylate superplasticizer.

In other embodiments of the invention, the cementitious composition additionally comprises a cement replacement. In other preferred embodiments of the invention, the cement replacement comprises a finely divided material that comprises a material whose particle size is less than about 75 microns. In certain preferred embodiments of the invention, the finely divided material comprises a finely divided limestone or a fine calcium carbonate. In other preferred embodiments of the invention, the finely divided material comprises a pozzolan, which, without intending to be limiting, reacts with water and the lime released from cement hydration to form densifying calcium silicates. In certain embodiments of the invention, the pozzolan may comprise any natural pozzolan; any artificial pozzolan, such as, for example, a fly ash; and any combination thereof. In yet other embodiments of the invention, the finely divided material comprises a ground slag, preferably, a ground granulated blast furnace slag.

In various embodiments of the invention, the cementitious compositions can include compounds or be compounded to demonstrate a number of advantageous features. In an embodiment of the invention, the cementitious compositions include compounds or are compounded to reduce the amount of water of convenience. In other embodiments of the invention, the cementitious compositions include certain compounds and are compounded in such a way so as to augment the effectiveness of a superplasticizer. In yet other embodiments of the invention, the cementitious compositions increase packing, or decrease intersticial spacing, of an aggregate that has been included in the composition, thereby effectively reducing permeability. In still yet other embodiments of the invention, the cementitious compositions include compounds or are compounded such that the cements that are included in the composition consume much of the water present, preferably in such a manner so as to reduce excessive production of reaction heat.

The inventive cementitious compositions, without intending to be bound by theory, offer improvements over other cementitious compositions known in the art by providing a hardened concrete that demonstrates a reduction in the amount of time needed to achieve a desired water vapor emission rate, otherwise known herein as an "attenuated water vapor emission." In an embodiment, the cementitious compositions will produce a hardened concrete that achieves a water vapor emission rate of 3 lb/1000 ft$^{2}$·24 hr in less than about 50 days; preferably, less than about 36 days; more preferably, less than about 28 days; and, even more preferably, less than about 22 days; and, still even more preferably, less than about 17 days.

In various embodiments of the invention, the cementitious compositions provide a reduction in the number of days needed to achieve an internal relative humidity of 75%. The cementitious compositions, according to certain embodiments of the invention, will produce a hardened concrete that has a 75% internal relative humidity in less than about 50 days; preferably, less than about 36 days; more preferably, less than about 28 days; and, even more preferably, less than about 22 days; and, still even more preferably, less than about 17 days.

In certain embodiments of the invention, the cementitious compositions offer the improvement of providing a finished concrete that allows the application of coatings and adhesives much sooner than concretes produced by conventional cementitious compositions known in the art.

In a preferred embodiment of the invention, the cementitious compositions are used to prepare a concrete structure for a flooring application. While not intending to be bound by theory, upon being mixed with water, the cementitious compositions consume and emit water in such a manner that little water remains in the hardened concrete to disturb water-based glues that are affixed to or coated onto the hardened concrete, which act as floor coverings.

The inventors have discovered that it is important not only to reduce the need for the amount of excess water to be added to the cementitious composition in preparing a cementitious mix, but to also include certain compounds in the formulation and to compound the formulation of the cementitious compositions in such a way that excess water is more favorably and rapidly removed than that which can be achieved by conventional cementitious compositions.

The cementitious compositions according to various embodiments of the invention are formulated by a proper selection of any combination of a binder and/or filler, including any pozzolan; an adjuvant and/or an additive; and an aggregate demonstrate an attenuated water vapor emission. Preferably, the cementitious compositions of the various embodiments of the invention will comprise a superplasticizer, even more preferably, a polycarboxylate superplasticizer. In a preferred embodiment of the invention, the cementitious composition comprises a cement replacement, more preferably, the cement replacement comprises a finely divided material, preferably, the finely divided material comprising at least one of a finely divided limestone or a fine calcium carbonate whose particle size is less than about 75 microns, a finely divided pozzolan and/or slag whose particle size is less than about 75 microns, and a finely divided highly reactive pozzolan whose particle size is less than about 75 microns.

In an embodiment of the invention, the cementitious composition includes a cement. In certain embodiments of the invention, the cement is any hydraulic cement. Non-limiting examples of hydraulic cements suitable for use in certain cementitious compositions include any class of Portland cement; masonry cement; alumina cement; refractory cement; magnesia cements, such as magnesium phosphate cement and magnesium potassium phosphate cement; calcium-based cements, such as calcium aluminate cement, calcium sulfoaluminate cement, and calcium sulfate hemi-hydrate cement; natural cement; hydraulic hydrated lime; any complex derivative thereof; and any combination thereof.

Aggregates useful in the inventive cementitious compositions include, but are not limited to, sand, stone, gravel, and any combination thereof. Aggregates are further classified as coarse aggregates that include, for example, gravel, crushed stone, or iron blast furnace slag, and fine aggregates, which is typically a sand. As non-limiting examples, stone can include limestone, granite, sandstone, brownstone, river rock, conglomerate, calcite, dolomite, serpentine, travertine, slate, bluestone, gneiss, quarizitic sandstone, quartzite, and any combination thereof.

Other specialty aggregates include heavyweight aggregates and lightweight aggregates. Heavyweight aggregates can include, but are not limited to, barite, magnetite, limonite, ilmenite, iron, and steel.

Common lightweight aggregates that are found in certain embodiments of the invention include, but are not limited to, slag, fly ash, silica, shale, diatomonous shale, expanded slate, sintered clay, perlite, vermiculite, and cinders. In certain embodiments of the invention, insulating aggregates may also be used. Non-limiting examples of insulating aggregates include pumice, perlite, vermiculite, scoria, and diatomite. In yet other embodiments of the invention, the cementitious composition may additionally comprise any of the aggregates selected from expanded shale, expanded slate, expanded clay, expanded slag, fumed silica, pelletized aggregate, processed fly ash, tuff, and macrolite. In still other embodiments of the invention, an aggregate may comprise a masonry aggregate non-limiting examples of which include shale, clay, slate, expanded blast furnace slag, sintered fly ash, coal cinders, pumice, and scoria.

In certain embodiments of the invention, an aggregate may comprise any combination of coarse aggregates and fine aggregates. Coarse aggregates are generally considered those aggregate materials retained on a number 4 sieve. Fine aggregates are generally considered those aggregate materials that pass through the number 4 sieve. For example, refer to ASTM C33 (2007), which supersedes ASTM C33 (2003), and ASTM C125 (2007), which supersedes ASTM C125 (2002) and ASTM C125 (2000a) standard specifications for concrete additives for a more comprehensive description of how to distinguish between fine aggregates and coarse aggregates.

In an embodiment of the invention, the cementitious composition comprises a cement replacement. In an embodiment of the invention, the cementitious composition comprises a cement replacement, the cement replacement comprising a finely divided material. In an embodiment of the invention, the finely divided material comprises a fine calcium carbonate. In a preferred embodiment of the invention, the fine calcium carbonate has a particle size of less than about 75 microns. In an embodiment of the invention, the finely divided material comprises limestone fines, and the cementitious composition has a ratio by weight of finely divided material to the total weight of the cementitious composition of from about 0.01 to about 1.0, from about 0.03 to about 0.8, from about 0.05 to about 0.8, from about 0.2 to about 0.8, and from about 0.3 to about 0.7. In other embodiments of the invention the cementitious composition has a ratio by weight of finely divided material to the total weight of the cementitious composition of from about 0.05 to about 0.4, and from about 0.1 to about 0.3. In a certain preferred embodiment of the invention, the cementitious composition has a ratio by weight of finely divided material to the total weight of the cementitious composition of from about 0.03 to about 0.8.

In an embodiment of the invention, the cement replacement may comprise a densifying precursor. As used herein, the term "precursor" refers to a compound, complex or the like that, after at least one of becoming chemically activated, becoming hydrated, or through at least one other preparation step becomes converted into a desired form to serve to further densify a concrete. In a preferred embodiment of the invention, the densifying precursor is a densifying calcium silicate precursor.

In an embodiment of the invention, the finely divided material comprises a pozzolan and/or a slag. In a preferred embodiment of the invention, the pozzolan and/or the slag have a particle size of less than about 75 microns. In another preferred embodiment of the invention, the pozzolan and/or slag have a particle size of less than about 45 microns. In an embodiment of the invention, the finely divided material comprises any of a pozzolan, such as, for example, a fly ash; a hydraulic addition, such as, for example, a ground granulated blast furnace slag; and any combination thereof, and the cementitious composition has a ratio by weight of finely divided material to total weight of the cementitious composition of from about 0.05 to about 0.8, from about 0.20 to about 0.80, and, preferably, from about 0.13 to about 0.75. In another embodiment of the invention, the finely divided material comprises a highly reactive pozzolan and the cementitious composition has a ratio by weight of finely divided material to total weight of the cementitious composition preferably of from about 0.05 to about 0.2, and, more preferably, from about 0.06 to about 0.10. In certain embodiments of the invention, the finely divided material comprises a pozzolan selected from the group consisting of any natural pozzolan; any artificial pozzolan, such as, for example, a fly ash; and any combination thereof.

In certain embodiments of the invention, the cementitious composition includes an admixture and/or additive including such admixtures or additives that function as accelerators, shrinkage reducing agents retarders, thickeners, tracers, air-entraining agents, air detraining agents, corrosion inhibitors, pigments, wetting agents, antifoaming and/or defoaming agents, any polymer that is water soluble, water repellants, fibers, damp proofing agents, gas formers, permeability reducers, pumping aids, viscosity control additives, other rheology modifying additives, fungicidal and/or germicidal agents, insecticidal agents, finely divided mineral admixtures, alkali-reactivity reducers, pH control agents and/or buffers, bonding admixtures, strength enhancing agents, shrinkage reduction agents, water reduction additives, and any mixture thereof.

In an embodiment of the invention, the cementitious composition comprises a cement, preferably, a hydraulic cement, having a concentration from about 10 wt % to about 80 wt %, and from about 25 wt % to about 70 wt % based on the total weight of the cementitious composition. In certain embodiments of the invention, the cementitious composition comprises a cement, preferably, a hydraulic cement, having a concentration from about 8 wt % to about 35 wt %, from about 10 wt % to about 30 wt %, from about 12 wt % to about 25 wt %, and from about 14 wt % to about 21 wt % based on the total weight of the cementitious composition.

In certain embodiments of the invention, the cementitious composition may additionally comprise, at least one of any aggregate, a pozzolan, and any combination thereof.

In an embodiment of the invention, the cementitious composition comprises a fine aggregate having a concentration from about 50 wt % to about 85 wt %, from about 60 wt % to about 80 wt %, and from about 65 wt % to about 75 wt % based on the total weight of the cementitious composition. In another embodiment of the invention, the aggregate comprises at least one fine aggregate and at least one coarse aggregate having a weight ratio of fine aggregate to total aggregate of from about 0.25 to about 1.00, from about 0.30 to about 0.75, from about 0.35 to about 0.65, from about 0.40 to about 0.55, and from about 0.40 to about 0.50.

In certain embodiments of the invention, the cementitious composition comprises a pozzolan, such as, for example, a fly ash; a ground granulated blast furnace slag; and any combination thereof having a concentration from about 5 wt % to about 30 wt %, from about 6 wt % to about 25 wt %, from about 7 wt % to about 20 wt %, and from about 13 wt % to about 17 wt % based on the total weight of the cementitious composition. In other embodiments of the invention, the cementitious composition comprises a highly reactive pozzolan, such as, for example, metakaolin, silica fume, and the like, including any combinations thereof, having a concentration from about 0.1 wt % to about 5 wt %, 0.5 wt % to about 2.5 wt %, and from about 1.0 wt % to about 2.0 wt % based on the total weight of the cementitious composition. In certain embodiments of the invention, a material selected from the group consisting of a pozzolan, a ground granulated blast furnace slag, and any combination thereof can be a very fine particulate material that reduces the voidage in the cementitious composition resulting in an improved moisture resistance of the finished concrete.

In certain embodiments of the invention, the cementitious composition comprises a fine calcium carbonate having a concentration from about 0.03 wt % to about 80 wt %, from about 0.05 wt % to about 25 wt %, from about 0.1 wt % to about 15 wt %, and, preferably, from about 0.13 wt % to about 7 wt % based on the total weight of the cementitious composition.

In other embodiments, the inventive cementitious composition comprises a dispersant. A non-limiting example of a dispersant includes any polycarboxylate dispersant, with or without polyether units. Polycarboxylate dispersants include those disclosed in U.S. Pat. Publ. No. 2008/0156225 to Bury, entitled "Rheology Modifying Additive for Cementitious Compositions," fully incorporated herein by reference. Dispersants may additionally include chemicals that function as any one of a plasticizer, a water reducer, a high range water reducer, a fluidizer, an antiflocculating agent, or a superplasticizer. Exemplary superplasticizers are disclosed in U.S. Pat. Publ. No. 2008/0087199 to Gartner, entitled "Cement Shrinkage Reducing Agent and Method for Obtaining Cement Based Articles Having Reduced Shrinkage," fully incorporated herein by reference. Dispersants may be selected that function as a superplasticizer.

In an embodiment of the invention, the cementitious composition further comprises a superplasticizer. Any superplasticizer disclosed herein or otherwise known in the art may be used in the cementitious compositions of various embodiments of the invention. In a preferred embodiment of the invention, the superplasticizer comprises a polycarboxylate admixture. A non-limiting example of a commercially available polycarboxylate superplasticizer includes GLENIUM®B 3000 available from BASF Corporation. GLENIUM 3000 comprises a polymer with a carbon backbone having pendant side chains with the characteristic that at least a portion of the side chains are attached to the carbon backbone through a carboxyl group or an ether group. GLENIUM 3000 is a liquid at ambient conditions having a specific gravity of approximately 1.08.

For example, using a cementious mix of 658 lb/yd$^3$ of Type III cement, slump of 6 inches, air content of 5-6%, concrete temperature of 65° F., and curing temperature of 65° F., it has been reported that GLENIUM 3000 provides a greater than 2 times increase in compressive strength in concrete after 8 hours of curing and an improvement of approximately 30% after 12 hours of curing compared to that of a conventional superplasticizer. For a cementitious mix of 658 lb/yd$^3$ of Type I cement, slump of 8-9 inches, non-air-entrained, concrete temperature of 70° F., dosage of admixtures adjusted to obtain 30% water reduction, GLENIUM 3000 has been shown to reduce the initial set time by as much as 2 hours and 33 minutes compared to that of a conventional superplasticizer.

In an embodiment of the invention, the superplasticizer is in the form of a liquid. In certain embodiments of the invention, the amount of superplasticizer added to the cementitious composition is from about 2 ounces to about 30 ounces, from about 4 ounces to about 24 ounces, from about 4 ounces to about 20 ounces, and from about 8 ounces to about 20 ounces for every 100 pounds of cementitious composition. In certain preferred embodiments of the invention, the superplasticizer added to the cementitious composition is from about 4 ounces to about 16 ounces, more preferably about 5 ounces to about 8 ounces, and, even more preferably, about 8 ounces for every 100 pounds of cementitious composition.

In an embodiment of the invention, the cementitious composition may comprise a water reducer. A non-limiting example of a water reducer admixture includes POLY-HEED® 997, an ASTM C494 type A water reducer, supplied by BASF Corporation. In certain embodiments of the invention, it is more preferred to use a water reducer with a superplasticizer in order to achieve a greater reduction in the amount of water mixed with the cementitious composition.

In an embodiment of the invention, the cementitious composition may additionally comprise prepuff particles such as those disclosed in U.S. Pat. Publ. No. 2008/0058446 to Guevare et al., entitled "Lightweight Concrete Compositions," fully incorporated herein by reference. In an exemplary embodiment, the prepuff particles are polymer particles having an average particle size of at least about 0.2 mm, at least about 0.3 mm, at least about 0.5 mm, at least about 0.9 mm, and at least about 1 mm up to at most about 8 mm, at most about 6 mm, at most about 5 mm, at most about 4 mm, at most about 3 mm, and at most about 2.5 mm.

As disclosed herein, the cementitious composition is combined with water, which functions as chemical water or hydration water and as excess water that, among other things, serves to plasticize the cementitious mix to render it more flowable. In preferred embodiments of the invention, the excess water, otherwise known as water of convenience, is minimized. While it is well-known in the art to include additives such as a plasticizer, more preferably a superplasticizer, in order to reduce the amount of water of convenience needed, conventionally, the dependence on excess water has not been entirely eliminated. For example, conventional cement mixtures tend to have water to cementitious ratios on the order of 0.4 or higher. Specialty formulations that include a superplasticizer have been disclosed that reduce the water to cementitious ratio to 0.25 or higher, for example, similar to those compositions disclosed in U.S. Pat. No. 6,858,074 to Anderson et al., entitled "High Early-Strength Cementitious Composition."

In certain embodiments, the cementitious compositions are combined with water having a water to cementitious ratio of less that about 0.5, less than about 0.4, less than about 0.35, less than about 0.3, and less than about 0.25. In certain embodiments of the invention, the cementitious compositions are mixed with water in a water to cementitious ratio of about 0.2 or higher. In preferred embodiments of the invention, the cementitious compositions are mixed with water in a water to cementitious ratio of from about 0.2 to about 0.25.

Another aspect of the invention provides methods of preparing cementitious compositions. In a preferred embodiment of the invention, a cementitious composition prepared according to certain embodiments of the invention is used to further prepare a concrete having an attenuated water vapor emission after curing or hardening. In a preferred embodiment of the invention, the cementitious composition is proportioned to achieve rapid drying, which can be measured, for example, by the ASTM test procedures for vapor emissions or internal relative humidity, as described herein. In certain other embodiments of the invention, the cementitious composition is proportioned to achieve a desired property of a hardened concrete, which preferably can be measured using any of the various inventive procedures defined herein.

In an embodiment of the invention, a method for preparing a cementitious composition comprises the steps of mixing a hydraulic cement with a cement replacement and adding a superplasticizer. In a preferred embodiment of the invention, the cementitious composition will be used to form a cementitious mix that produces a concrete having an attenuated water vapor emission upon hardening.

In an embodiment of the invention, the cement replacement comprises a finely divided material. In an embodiment of the invention, the finely divided material has a particle size of less than about 75 microns. For example, a finely divided material having a particle size of less than about 75 microns may be the material retained on a standard sieve having 75 micron openings. Alternatively, a finely divided material having a particle size of less than about 75 microns may be the material that passes through a standard sieve having a varying plurality of openings of +/−75 micron. In another embodiment of the invention, the finely divided material has a particle size of less than about 45 microns. In yet another embodiment of the invention, the finely divided material comprises a material that passes through a standard sieve size of 200.

In an embodiment of the invention, the finely divided material comprises a fine calcium carbonate. In another embodiment of the invention the finely divided material comprises limestone fines, the limestone fines comprising calcium carbonate. Further to this embodiment, the cementitious composition has a ratio by weight of finely divided material to the total weight of the cementitious composition of from about 0.03 to about 0.8, and, alternatively, from about 0.05 to about 0.4.

In another embodiment of the invention, the finely divided material is selected from the group consisting of a pozzolan, such as, for example, a fly ash; a ground granulated blast furnace slag; and any combination thereof. Further to this embodiment, the cementitious composition has a ratio by weight of finely divided material to total weight of the cementitious composition of from about 0.03 to about 0.8, and, alternatively, from about 0.15 to about 0.8.

In still another embodiment of the invention, the finely divided material comprises a highly reactive pozzolan selected from the group consisting of silica fume, metakaolin, and any combination thereof. Further to this embodiment, the cementitious composition has a ratio by weight of finely divided material to cement of from about 0.05 to about 0.20.

In certain embodiments of the invention, the cement replacement comprises a densifying precursor. In a preferred embodiment of the invention, the densifying precursor is a densifying calcium silicate precursor.

In an embodiment of the invention, the superplasticizer has a concentration in a range from about 4 ounces to about 20 ounces for every 100 pounds of the total weight of the cementitious composition. In a preferred embodiment of the invention, the superplasticizer includes a polycarboxylate superplasticizer.

In an embodiment of the invention, the method for preparing a cementitious composition additionally comprises the step of incorporating an aggregate in the cementitious composition. In an embodiment of the invention, the aggregate comprises at least one of a fine aggregate, a course aggregate, and combinations thereof.

In another embodiment of the invention, a method for preparing a cementitious composition comprises the steps of mixing a hydraulic cement with a pozzolan and an aggregate and adding an admixture comprising a superplasticizer. In a preferred embodiment of the invention, the cementitious composition will be used to prepare a cementitious mix that produces a concrete having an attenuated water vapor emission upon hardening.

Another aspect of the various embodiments of the invention provides a cementitious mix comprising any of the cementitious compositions. In a certain embodiments of the invention, the cementitious mix comprises an amount of water sufficient to provide a water to cementitious ratio of from about 0.05 to about 0.6; from about 0.1 to about 0.5; preferably, from about 0.2 to about 0.4; and, more preferably, from about 0.25 to about 0.35.

In certain embodiments of the invention, the cementitious mix comprises a hydraulic cement, an aggregate, a cement replacement, water, and a superplasticizer. In a preferred embodiment of the invention, the cement replacement is a densifying calcium silicate precursor. In another preferred embodiment of the invention, the superplasticizer is a polycarboxylate superplasticizer.

According to certain embodiments of the invention, the cementitious mix comprises a hydraulic cement having a concentration from about 10 wt % to about 30 wt % based on a total weight of cementitious compounds; an aggregate having a concentration from about 25 wt % to about 70 wt % based on the total weight of cementitious compounds; a densifying calcium silicate precursor having a concentration from about 3 wt % to about 80 wt % based on the total weight of cementitious compounds; an amount of water sufficient to provide a water to cementitious ratio of from about 0.2 to about 0.4; and a polycarboxylate superplasticizer having a concentration from about 4 ounces to about 16 ounces per 100 pounds of cementitious compounds.

In an exemplary embodiment of the invention, the cementitious mix comprises a hydraulic cement having a concentration from about 10 wt % to about 30 wt % based on a total weight of cementitious compounds; an aggregate having a concentration from about 25 wt % to about 70 wt %, preferably, from about 45 wt % to about 65 wt % based on the total weight of cementitious compounds; a densifying calcium silicate precursor having a concentration from about 3 wt % to about 80 wt %, preferably, from about 5 wt % to about 25 wt % based on the total weight of cementitious compounds; an amount of water sufficient to provide a water to cementitious ratio of from about 0.2 to about 0.4; and a polycarboxylate superplasticizer having a concentration from about 4 ounces to about 16 ounces per 100 pounds of cementitious compounds. In another embodiment of the invention, the polycarboxylate superplastizer has a concentration of from about 5 ounces to about 8 ounces per 100 pounds of cementitious compounds. In a preferred embodiment of the invention, the cementitious mix is used to prepare a concrete having an attenuated water vapor emission.

Another aspect of various embodiments of the invention provides methods of preparing a concrete structure using cementitious compositions to form a hardened concrete having an attenuated water vapor emission upon hardening. In an embodiment of the invention, a particular curing regimen may be applied to poured cementitious mix that allows any excess water to be more quickly emitted or dissipated as the concrete cures or hardens resulting in a reduced or an attenuated water vapor emission after hardening.

In an embodiment of the invention, a method for preparing a concrete structure using a cementitious composition comprises the steps of mixing a hydraulic cement with a cement replacement, adding an admixture comprising a superplasticizer, and blending an amount of water into the cementitious composition to prepare a cementitious mix. In a preferred embodiment of the invention, the cementitious mix will produce a hardened concrete having an attenuated water vapor emission.

In yet another embodiment of the invention, a method for preparing a concrete structure using a cementitious composition comprises the steps of providing the cementitious composition having a hydraulic cement, a cement replacement, and a superplasticizer; and blending an amount of water into the cementitious composition to prepare a cementitious mix. In a preferred embodiment of the invention, the cementitious mix will produce a hardened concrete having an attenuated water vapor emission.

Generally, the method of using the cementitious composition additionally comprises the steps of using the cementitious mix to form a cementitious segment or a preform of the concrete structure and curing the cementitious segment or preform of the concrete structure to a hardened concrete. Further to this embodiment, the cementitious segment may be further processed. For example, a trowel may be applied to the cementitious segment to, for example, smooth the surface of the cementitious segment and/or to even the distribution of the cementitious mix in a form.

In certain embodiments, the methods of use may additionally comprise the step of applying a regime and/or technique that facilitates a more rapid curing of the cementitious mix to a hardened concrete. Any technique known in the art may be used to more rapidly cure the cementitious mix. Non-limiting examples of such techniques include applying a moisture barrier between a moisture source and the formed cementitious segment; maintaining the movement of air at the surface of the cementitious segment being cured to ensure water that evolves from the segment is removed; heating, for example, with thermal and/or radiant heat, the cementitious segment being cured; and controlling humidity between the moisture barrier and the formed cementitious segment by the maintaining and heating steps.

In an embodiment of the invention, the cement replacement comprises a finely divided material. In certain embodiments of the invention, the finely divided material has a particle size of less than about 75 microns. In an embodiment of the invention, the finely divided material is a material that passes through a standard sieve size of 200.

In a preferred embodiment, the finely divided material comprises a cement replacement. In an embodiment of the invention, the finely divided material comprises a fine calcium carbonate. In another embodiment of the invention the finely divided material comprises limestone fines, the limestone fines comprising calcium carbonate. Further to this embodiment, the cementitious composition has a ratio by weight of finely divided material to the total weight of the cementitious composition of from about 0.03 to about 0.8, more preferably, from about 0.07 to about 0.4.

In another embodiment of the invention, the finely divided material is selected from the group consisting of a pozzolan, such as, for example, a fly ash; a ground granulated blast furnace slag; and any combination thereof. Further to this embodiment, the cementitious composition has a ratio by weight of finely divided material to cement of from about 0.15 to about 0.8.

In still another embodiment of the invention, the finely divided material comprises a highly reactive pozzolan selected from the group consisting of silica fume, metakaolin, and any combination thereof. Further to this embodiment, the cementitious composition has a ratio by weight of finely divided material to cement of from about 0.06 to about 0.105.

In certain embodiments of the invention, the cement replacement comprises a densifying precursor. In a preferred embodiment of the invention, the densifying precursor is a densifying calcium silicate precursor.

In an embodiment of the invention, the superplasticizer has a concentration in a range from about 4 ounces to about 20 ounces for every 100 pounds of cementitious composition. In a preferred embodiment of the invention, the superplasticizer at least includes a polycarboxylate superplasticizer.

In a preferred embodiment of the invention, the amount of water blended into the cementitious composition is minimized to an amount that is sufficient to hydrolyze the cementitious composition and allow the prepared cementitious mix to achieve a desired level of plasticity. In another preferred embodiment of the invention, the amount of water blended into the cementitious composition, the concentration of the superplasticizer, and the ratio by weight of the finely divided material to the cement are proportioned to achieve a desired level of plasticity while achieving a desired property of the concrete. In certain embodiments, the desired property of the concrete is any of minimizing an amount of time needed to achieve a water vapor emission of the hardened concrete, minimizing an amount of time needed to achieve an internal relative humidity of the hardened concrete, a reduced shrinkage of the hardened concrete, and a maximum heat of hydration. Preferably, a reduced shrinkage of the concrete will reduce the curling or warping of the concrete when used in flooring applications and allow for better control of joint spacing between concrete segments.

In an embodiment of the invention, the method for preparing a cementitious composition additionally comprises the step of incorporating an aggregate into the cementitious composition. In an embodiment of the invention, the aggregate comprises at least one of a fine aggregate, a course aggregate, and any combination thereof.

In another embodiment of the invention, a method for preparing a cementitious composition comprises the steps of mixing a hydraulic cement with a pozzolan and an aggregate, adding an admixture comprising a superplasticizer, and blending an amount of water into the cementitious composition to prepare a cementitious mix. In a preferred embodiment of the invention, the cementitious mix will produce a hardened concrete having an attenuated water vapor emission.

The combination of steps for preparing a cementitious composition for use in preparing a concrete structure may be varied depending upon the desired application of the finished concrete structure. For example, in many circumstances, a concrete structure used in flooring must assure that a dry substrate be available to which a coating and/or sealant is applied. While not intending to be limiting, the compositions and methods of the invention are suitable to such applications because they provide a relatively fast drying cementitious mix with an attenuated or reduced water vapor emissions after cure. Typically, the cementitious mixes for such applications are typically characterized by an appropriate mix of cementitious compounds—i.e., cement(s), slag(s), and/or pozzolans—available to react with the residual water allowing the water vapor emissions to be reduced to about 3 lb/1000 ft$^{2}$·24 hr and an internal relative humidity of about 75% to be achieved in 45 days. The rule-of-thumb for more conventional compositions is 1 month for every inch of concrete thickness (e.g., 5 months for a commonly used 5 inch concrete structure).

As disclosed herein, the critical parameters for achieving a relatively fast drying concrete using the cementitious compositions of the inventions and methods as disclosed herein include water to cementitious ratio, employing a curing technique that is adequate to assure eventual water impermeability, and the use of a sufficiently fine material to create a dense mass.

As further disclosed herein, care must be exercised in blending any pozzolan in order to control the heat of hydration, or else thermal cracking of the concrete could become problematic rendering, for the most part, the use of any pozzolan virtually ineffective. Care must also be exercised in proportioning and compounding the cementitious mix. For example, a cementitious mix that is too sticky will be difficult to pump and finish using conventional techniques.

Another aspect of various embodiments of the invention provides a testing protocol or procedure for estimating the amount of water vapor emissions from a concrete after hardening. Preferably, such a protocol relies upon the use of smaller, more manageable sample panels and provides results more quickly than waiting for a sample panel of the concrete to become hardened and achieve a desired water vapor emission. In other embodiments, a testing protocol is provided for determining the internal relative humidity of the concrete. The inventive testing protocol may additionally be referred to herein as the mortar method.

In an embodiment of the invention, a method for estimating the water vapor emission from a hardened concrete comprises the steps of preparing a mortar mixture that is representative of the cementitious mix used to prepare the concrete, casting the mortar mixture into a sample; optionally, curing the sample; equilibrating the sample in a chosen or selected environment, calculating a daily weight loss from the sample, and estimating the water vapor emission using an established correlation based on the daily weight loss of the sample. In certain embodiments, the conditions of the environment are selected to represent the same or similar conditions where the concrete structure is to be formed. Exemplary environmental conditions that may be controlled include, but are not limited to, pressure (typically at or near atmospheric pressure), humidity, and temperature.

The steps of the procedure for estimating the water vapor emission of hardened concrete may also be used to estimate other properties of a concrete. Such other properties include, but are not limited to, an internal relative humidity, a required amount of water content of the concrete, and the required water to cementitious ratio. Of course, the daily weight loss of the sample will be used to estimate any of these other properties based upon a correlation that has been established for these properties.

In an embodiment of the invention, the mortar mixture that is representative of the cementitious mix comprises the compounds present in the cementitious mix except that the mortar mixture is substantially free of any coarse aggregate. In a preferred embodiment of the invention, the compounds of the mortar mixture will have the same ratios as those of the compounds of the cementitious mix.

In an embodiment of the invention, the procedure for preparing a mortar mixture comprises the steps of combining a sufficient amount of the water with an admix, adding a sand, and continuing to add any remaining water as the compounds continue to be mixed. In a preferred embodiment, water continues to be added to achieve a target and/or desired workability.

In an embodiment of the invention, the sample has a surface to volume ratio of from about 0.4 in$^{-1}$ to about 1.0 in$^{-1}$, from about 0.5 in$^{-1}$ to about 0.9 in$^{-1}$, from about 0.6 in$^{-1}$ to about 0.8 in$^{-1}$, and, preferably, from about 0.64 in$^{-1}$ to about 0.7 in$^{-1}$. In a preferred embodiment of the invention, the sample is cast to a depth that at least represents the temperature and/or moisture gradient that develops for a concrete exposed to atmospheric conditions. In a preferred embodiment of the invention, the depth of the sample is from about 1⅜ inches to about 1⅝ inches. In certain embodiments of the invention, the depth of the sample is greater than about 1⅜ inches, with the depth of the sample greater than about 1½ inches being the most preferred.

In an embodiment of the invention, the step of curing the sample comprises the steps of sealing the sample to prevent water and any other vapor loss and curing the sample for a period of time. In other embodiments of the invention, the step of curing the sample comprises the steps of not sealing the sample for a predetermined period of time to initially facilitate water and any other vapor loss, subsequently sealing the sample, and curing the sample for a period of time. In certain embodiments of the invention, the period of time for curing the sample is at least about 1 day, at least about 2 days, at least about 5 days, at least about 7 days, at least about 10 days, at least about 14 days, at least about 20 days, at least about 21 days, at least about 25 days, and at least about 28 days. Further to this embodiment of the invention, any curing step that involves sealing the sample additionally comprises the step of unsealing the sample, preferably, prior to the equilibrating step.

In a preferred embodiment of the invention, any of the methods for estimating water vapor emission from a hardened concrete are performed to at least one of identify one or more compounds to include in the cementitious composition to achieve a desired water vapor emission from a hardened concrete, identify how the compounds of the cementitious composition should be proportioned to achieve a desired water vapor emission from a hardened concrete, identify one or more compounds to include in the cementitious mix to achieve a desired water vapor emission from a hardened concrete, identify how the compounds of the cementitious composition should be proportioned to achieve a desired water vapor emission from a hardened concrete, and identify an attenuated water vapor emission of a hardened concrete based on any one of the compound formulation of the cementitious composition, the proportioning of the compounds of the cementitious composition, the compound formulation of the cementitious mix, the proportioning of the compounds of the cementitious mix, and any combination thereof. A person with ordinary skill in the art having the benefit of this disclosure understands that the methods, according to various embodiments of the invention, for estimating water vapor emissions from a hardened concrete may be useful for evaluating any factor, procedure, or parameter that otherwise may influence the water vapor emission rate of a hardened concrete. The mortar method may additionally be applied in comparative testing of various amounts and types of sands, slags, pozzolans, and cements.

A person having ordinary skill in the art having the benefit of this disclosure will recognize the mortar method has several advantages over conventional testing protocols known in the art for determining the water vapor emission or the internal relative humidity of a hardened concrete. For example, the test panels of the mortar method are smaller than the larger test panels used for the conventional techniques. Additionally, the mortar method offers a much quicker turnaround of results over the conventional techniques which typically rely upon waiting for the full extent of duration of curing and hardening of the concrete.

The inventive analytical procedure for more quickly estimating drying rates can be preferred over the ASTM F1869 calcium chloride test, which measures the amount of water vapor emitted by the concrete in a secondary manner by evaluating the change in chloride weight. The inventive analytical procedure is also preferred, in certain embodiments, because of its use of smaller quantities of mortar ingredients and the samples have a reduced size over conventional samples. Many conventional tests operate on much larger concrete panels that can weigh up to approximately 250 pounds. The samples of the inventive procedure weight approximately 4 pounds. Without intending to be bound by theory, the mortar method is preferred, in certain embodiments of the invention, because it creates a technician friendly, easy to use test method to quickly facilitate the determination of water vapor emissions from a hardened concrete mixture.

The mortar method allows the sample specimens to be sized such that the base mortar quantity is $1/454$ of a cubic yard. This allows the weights of selected compounds to be directly converted to an equivalent amount in gram weight in order to allow convenient laboratory batching.

In an embodiment of the invention, a method for estimating a slump of a cementitious mix comprises the steps of portioning a mortar mixture into two layers in an ASTM C128 cone, rodding each of the two layers of the mortar mixture, leveling the surface of the mortar mixture, lifting the cone free of the mortar, determining a slump of the mortar mixture in increments of a predefined length, and estimating a slump of a cementitious mix, which corresponds to the mortar mix, by dividing the number of increments by a conversion factor. In an embodiment of the invention, the predefined length of an increment is about $1/16$ inch. In an embodiment of the invention, the conversion factor used in the method for estimating the slump of cementitious mix is about 4.

In an embodiment of the invention, a method for estimating a volume yield of a cementitious mix comprises the steps of portioning a mortar mixture into two layers of an ASTM C185 volumetric cylinder, rodding each of the two layers of the mortar mixture, consolidating each layer of the mortar mixture, leveling the surface of the mortar mixture, and calculating the volume yield by dividing the net weight of the mortar mixture in the volumetric cylinder into the actual batch weight used to prepare the mortar mixture and multiplying by the volume the mortar mixture occupies in the volumetric cylinder. In an embodiment of the invention, the method for estimating a volume yield of a cementitious mix additionally comprises the step of calculating an amount of air in the mortar mixture by subtracting a volume of the solids from the volume yield.

In certain preferred embodiments of the invention, any of the methods of the invention for estimating the properties of the concrete and/or the cementitious mix are implemented, at least in part, in one or more analytical devices for purposes of supporting assessing any of the properties of a hardened concrete and/or a cementitious composition, as further described herein. An exemplary analytical device may comprise at least one of manually and automatically inputting information needed to perform the estimation into the analytical device, a processing unit for calculating the estimated property or properties, and an output device for providing the results of the estimation procedure. In certain embodiments of the invention, the results of the estimation procedure may be used to provide recommendations on how to change the compounds in the formulation or how the compounds of the formulation should be proportioned and/or prepared in order to achieve a more desirable property result.

EXAMPLES

Example 1

The purpose of the tests in EX. 1 were to determine whether the water vapor emissions from prepared mortar samples determined by the mortar method are related to the water vapor emissions from concrete determined by a conventional test procedure. The tests were conducted on a cementitious sample prepared according to the compositions in Table 1.

TABLE 1

|  | Amount | Volume |
|---|---|---|
| Cement | 300 g | 95.2 cc |
| Slag | 500 g | 170.0 cc |
| Sand | 1,500 g | 570.3 cc |
| Water | 225 g | 225.0 cc |
| Admixture | 100 oz | 5.4 cc |

The composition to be used in the mortar method is prepared by placing a cement, a portion of the water, and an admixture in the bowl of a Hobart 5 quart mixer and mixed at a slow speed for one minute. Sand is added and mixing is continued at a slow speed for one additional minute. The mixer is stopped and the sides and bottom of the bowl are scraped to insure that all material is in the mix and has not segregated on the side of the bowl. Mixing is continued at a slow speed for two additional minutes while gradually adding the remaining water until the desired consistency is reached. Mixing continues for an additional 30 seconds after the last amount of water is added. Total mix time should not exceed 10 minutes.

Portions of the mix are placed in a sand cone, for example, an ASTM C127 cone, in two layers, and each layer is rodded 25 times using a ¼ inch rod. The cone top is used to strike the surface level and the cone is lifted free of the mortar in 5 seconds. The slump of the mortar is measured relative to the original heights in $\frac{1}{16}^{th}$ inch increments. The number of $\frac{1}{16}^{th}$ inch increments is divided by 4 to estimate the slump in normally proportioned concrete in inches. (E.g., $20\frac{1}{16}^{th}$ inch increments in slump in the mortar equals a potential for 5 inches of slump in the corresponding concrete.)

A colloid defoamer is used, as needed, to control the flare in mortar air accompanying doses of some admixtures or cements. Without the use of this additive, admixture evaluations and cement comparatives may become disproportionately influenced by air contents that are atypical of that produced in concrete. Typically, it is better to run most comparatives on a same low air basis.

A portion of the mortar is placed in a 400 cc ASTM C 185 volumetric cylinder in two layers with each layer rodded 25 times using a ¼ inch rod. Each layer is consolidated by rapping the container on the casting surface several times. The cup is used to strike off the surface level. The volume yield of the mix including air is calculated by dividing the net weight of the cup mortar into the actual batch weights and multiplying the result by the 400 cc (the container volume), which should also be the volume the mortar mixture occupies in the container. The air content of the mixture may be calculated by subtracting the expected volume of the solid based upon the gravities of each of the different compounds used in the mixture from the actual volume of the mixture. All of the material is placed back into the mixer and remixed for 30 seconds. The composition is not retempered.

The mortar is placed in the 886 cc mold and consolidated by rapping the filled mold several times on the casting surface until the mortar is level and uniform in appearance. The casting is weighed to the nearest 0.1 gram on a scale. The cure regimen normally involves sealing a specimen against water and vapor loss for 7 days; however, other routines may be utilized if needed. At the end of the cure cycle, the specimen is again weighed and placed in an environment where it is allowed to attain equilibrium.

Each specimen is weighed every 24 hours in order to create a water vapor loss record. The results for two panels from four different samples are shown in Table 2.

TABLE 2

|  | Sample 1 | | Sample 2 | | Sample 3 | | Sample 4 | |
|---|---|---|---|---|---|---|---|---|
| Date | Test A, gr | Test B, gr | Test A, gr | Test B, gr | Test A, gr | Test B, gr | Test A, gr | Test B, gr |
| 1-Sep | 2,013.9 | 1,945.5 | 2,027.8 | 2,180.7 | 2,012.8 | 1,987.7 | 1,635.3 | 1,844.7 |
| 14-Sep | 1,989.9 | 1,916.4 | 2,011.9 | 2,169.1 | 1,997.9 | 1,975.0 | 1,604.2 | 1,812.4 |
| 19-Sep | 1,988.1 | 1,914.4 | 2,010.2 | 2,167.8 | 1,997.1 | 1,974.3 | 1,601.2 | 1,809.5 |
| 23-Sep | 1,987.2 | 1,913.4 | 2,009.5 | 2,167.2 | 1,997.0 | 1,974.2 | 1,599.7 | 1,807.8 |
| 28-Sep | 1,986.2 | 1,912.0 | 2,008.3 | 2,166.5 | 1,996.7 | 1,974.0 | 1,598.0 | 1,805.9 |
| Δ Loss | 27.7 | 33.5 | 19.5 | 14.2 | 16.1 | 13.7 | 37.3 | 38.8 |

The corresponding sample data for the 2 foot×2 foot panels tested in CC tents, which included the coarse aggregate, are shown in Table 3.

TABLE 3

| Date | Sample 1 Vapor Loss, cc | Sample 2 Vapor Loss, cc | Sample 3 Vapor Loss, cc | Sample 4 Vapor Loss, cc |
|---|---|---|---|---|
| 1-Sep | start | start | start | start |
| 9-Sep | 9.1 | 7.7 | 6.8 | 11.3 |
| 12-Sep | 7.8 | 6.4 | 5.8 | 9.9 |
| 16-Sep | 7.2 | 5.8 | 5.3 | 9.2 |
| 19-Sep | 6.3 | 5.6 | 4.9 | 8.1 |
| 22-Sep | 6.0 | 4.5 | 4.6 | 7.6 |
| 26-Sep | 5.8 | 3.7 | 4.4 | 7.2 |
| 29-Sep | 5.2 | 3.9 | 4.1 | 7.3 |
| 3-Oct | 4.7 | 3.7 | 3.7 | 6.3 |
| 6-Oct | 4.2 | 3.2 | 3.1 | 5.6 |
| 17-Oct | 3.9 | 3.2 | 3.1 | 5.2 |
| 20-Oct | 3.7 | 3.0 | 2.9 | 5.0 |

FIG. 1 graphically illustrates the total small panel water loss of the mortar samples against the corresponding water vapor loss by the 2 foot×2 foot sample panels of an associated concrete. The weight loss on the 6 inch×6 inch×1½ inch sample specimens appear to be directly related to the vapor emissions from a 2 foot×2 foot×5 inch concrete sample using the same mortar proportions. With additional sample testing, a relationship may be developed that will allow the results from the shorter, small panel tests to be used to estimate the water vapor emissions from the hardened concrete.

Examples 2-3

The purpose of the tests in EX. 2 were to demonstrate the effect of the concentration of a polycarboxylate superplasticizer and the use of a water reducer on the use of chemically bound water and the extent of shrinkage realized by the concrete sample mixes of Table 4.

TABLE 4

| Compound/Property | Sample 5 | Sample 6 Concrete Mix | Sample 7 |
|---|---|---|---|
| Portland Cement, Type I-II, lb | 800 | 517 | 611 |
| Sand, ASTM C33, lb | 1,300 | 1,525 | 1,500 |
| 1 inch Stone, ASTM C33, lb | 1,850 | 1,850 | 1,850 |
| GLENIUM 3000, oz/100 lb cement | 16.0 | — | 8.0 |
| POLYHEED 997, oz/100 lb cement | — | 5.3 | — |
| Water, lb | 225 | 290 | 228 |
| water to cement ratio | 0.28 | 0.56 | 0.37 |
| Air Content, % | 1.7 | 3.4 | 5.4 |
| Density, lb/ft$^3$ (pcf) | 155 | 147 | 148 |
| Yield, ft$^3$/yd$^3$ | 26.9 | 28.1 | 28.1 |
| Slump, inches | >6.00 | 4.25 | 5.25 |

The data in Table 5 shows the shrinkage results for the concrete mixes of the examples. The specimens were tested according to the ASTM C157 (2006) protocol. Each shrinkage sample was cured at 73° F. and 100% humidity for 24 hours, and followed by a curing step while immersed in water for 7 days. Drying was conducted at 50% relative humidity and 73° F.

TABLE 5

| Days Drying | Sample 5 | Sample 6 Shrinkage, % | Sample 7 |
|---|---|---|---|
| 14 | 0.0133 | 0.0193 | 0.0133 |
| 21 | 0.0203 | 0.0290 | 0.0183 |
| 28 | 0.0227 | 0.0343 | 0.0217 |
| 35 | 0.0243 | 0.0387 | 0.0230 |
| 42 | 0.0303 | 0.0487 | 0.0300 |
| 56 | 0.0350 | 0.0560 | 0.0353 |

The cementitious composition of sample 6, which uses a water reducer instead of a polycarboxylate superplasticizer shows the greatest amount of shrinkage. The cementitious compositions of samples 5 and 7 show that the amount of shrinkage can be somewhat maintained with varying concentrations of cement in the composition by changing the proportion of superplasticizer to control the water.

The purpose of the test in EX. 3 was to show that the need for additional water with an increasing concentration of cement in a cementitious composition can be offset by increasing the use of a superplasticizer and also by increasing the concentration of the superplasticizer in the cementitious composition. As the sample mixes illustrated in Table 4 show, sample 7 has 94 lbs more concrete than sample 6, and yet has a much smaller demand for water as a result of using a superplasticizer versus that of using a water reducer. Sample 5 contains 189 lbs more cement than sample 7 and yet has a lower water to cementitious ratio as are result of increasing the concentration of superplasticizer in the cementitious composition.

Example 4

The purpose of the tests in EX. 4 were to demonstrate the effect of a polycarboxylate superplasticizer on the reduction in the amount of time needed to achieve a desired rate of water vapor emissions using the concrete sample mixes of Table 6.

TABLE 6

| Compound/Property | Sample 8 | Sample 9 Concrete Mix | Sample 10 |
|---|---|---|---|
| Portland Cement, Type I-II, lb | 800 | 517 | 611 |
| Sand, ASTM C33, lb | 1,300 | 1,525 | 1,500 |

TABLE 6-continued

| Compound/Property | Sample 8 | Sample 9 Concrete Mix | Sample 10 |
|---|---|---|---|
| 1 inch Stone, ASTM C33, lb | 1,850 | 1,850 | 1,850 |
| GLENIUM 3000, oz/100 lb cement | 16.0 | — | 8.0 |
| POLYHEED 997, oz/100 lb cement | — | 5.3 | — |
| Water, lb | 225 | 281 | 228 |
| water to cement ratio | 0.28 | 0.54 | 0.37 |
| Air Content, % | 3.4 | N/A | 5.6 |
| Density, lb/ft$^3$ (pcf) | 155 | 146 | 147 |
| Yield, ft$^3$/yd$^3$ | 27.0 | 28.2 | 28.2 |
| Slump, inches | >6.00 | 4.50 | 5.00 |

The curing data and number of days required to achieve a water vapor emission rate of 3 lb/1000 ft$^2$·24 hr shown in Table 7 were obtained by casting each of the samples in a 2 foot×2 foot×5½ inch deep panel lined with polyethylene. Immediately prior to initial set, each panel was given a steel trowel finish and sealed for the noted cure period at 73° F. Following the cure period, the concrete slabs were unsealed and allowed to dry at 50% relative humidity and 73° F. in a drying room. The water vapor emissions data was obtained by averaging two calcium chloride dome tests conducted according to the ASTM F1869 test standard.

TABLE 7

| | Sample 8 | Sample 9 | Sample 10 |
|---|---|---|---|
| Curing Time, days | 28 | 28 | 28 |
| Drying Time needed for 3 lb/1000 ft$^2$·24 hr Emissions, days | 17 | >50 | 22 |

The mixture of sample 9 has a water to cementitious ratio that is greater than that of samples 8 and 10; however, the sample requires greater than 50 days drying in order to achieve a water vapor emissions rate of 3 lb/1000 ft$^2$·24 hr. The mix of sample 7 shows a superplasticizer helps to attenuate the water vapor emissions over that of the water reducer used in the mix of sample 9. Sample 8 shows that increasing the concentration of the superplasticizer further reduces the amount of drying time needed to achieve the desired water vapor emissions rate.

Example 5

The purpose of the tests in EX. 5 were to demonstrate the effect of a polycarboxylate superplasticizer along with the presence of a reactive pozzolan on the amount of time needed to reduce the internal relative humidity to a desired value using the concrete sample mixes of Table 8.

TABLE 8

| Compound/Property | Sample 11 | Sample 12 Concrete Mix | Sample 13 |
|---|---|---|---|
| Hanson Cement, Type I-II, lb | 517 | 740 | 740 |
| Silica Fume, lb | — | 60 | — |
| Metakaolin, lb | — | — | 60 |
| Sand, ASTM C33, lb | 1,525 | 1,200 | 1,200 |
| Sand, ASTM C33 #67, lb | 1,950 | 1,950 | 1,950 |
| GLENIUM 3000, oz/100 lb cement | — | 16.2 | 16.2 |
| POLYHEED 997, oz/100 lb cement | 5.0 | — | — |
| Colloid Defoamer, oz | 0.5 | 0.5 | 0.5 |
| Water, lb | 264 | 186 | 197 |
| water to cement ratio | 0.51 | 0.23 | 0.25 |
| Mix Temperature, ° F. | 65 | 66 | 67 |
| Air Content, % | 1.3 | 3.6 | 1.1 |
| Density, lb/ft$^3$ (pcf) | 152 | 156 | 156 |

TABLE 8-continued

| Compound/Property | Sample 11 | Sample 12 Concrete Mix | Sample 13 |
|---|---|---|---|
| Yield, ft³/yd³ | 28.1 | 26.5 | 26.7 |
| Slump, inches | 5.75 | flowing | flowing |

Each sample was cast in a 2 foot×2 foot×5½ inch deep panel lined with polyethylene. Immediately prior to initial set, each panel was given a steel trowel finish and sealed for a 13-day cure period at 73° F. Following the cure period, the concrete slabs were unsealed and allowed to dry at 50% relative humidity and 73° F. in a drying room. The relative humidity was obtained according to the ASTM F 2170 test procedure using in situ probes. The curing data and number of days required to achieve an internal relative humidity of 75% for the cured concrete samples are shown in Table 9.

TABLE 9

|  | Sample 11 | Sample 12 | Sample 13 |
|---|---|---|---|
| Curing Time, days | 13 | 13 | 13 |
| Drying Time needed to Achieve 75% Relative Humidity, days | >63 | 28 | 28 |

The cementitious composition of sample 11, which used only the water reducer, produced a concrete having an internal relative humidity of 87.3% at the end of 63 days. Samples 12 and 13 comprising silica fume and metakaolin, respectively, as well as a superplasticizer produced a concrete that required only 28 days of drying time to achieve an internal relative humidity of 75%.

Example 6

The purpose of the tests in EX. 6 were to demonstrate the effect of partial substitution with a finely divided material (finely divided limestone) generally smaller than a U.S. standard sieve size 200. The sieve produced a finely divided material having a particle size of less than about 75 microns. #3 limestone fines represent a finely divided reactive material, the ASTM C33 sand is a fine aggregate, and the Cupertino lime is a coarse aggregate. Samples 14, 15, and 16 of Table 10 also include a superplasticizer.

TABLE 10

| Compound/Property | Sample 14 | Sample 15 | Sample 16 | Sample 17 |
|---|---|---|---|---|
| Cement, lb | 500 | 500 | 800 | 500 |
| #3 Limestone Fines, lb | — | 270 | — | — |
| Sand, ASTM C33, lb | 1,700 | 1,510 | 1,450 | 1,470 |
| Cupertino Lime, St. ¾, lb | 1,800 | 1,800 | 1,800 | 1,800 |
| GLENIUM 3000, oz/100 lb cement | 16 | 16 | 16 | — |
| POLYHEED 997, oz/100 lb cement | — | — | — | 5 |
| Water, lb | 213 | 172 | 200 | 269 |
| water to cement ratio | 0.43 | 0.34 | 0.25 | 0.54 |
| Mix Time, min | 20 | 17 | 14 | 10 |
| Mix Temperature, ° F. | 82 | 86 | 89 | 88 |
| Density, lb/ft³ (pcf) | 153 | 157 | 157 | 150 |
| Yield, ft³/yd³ | 27.5 | 27.1 | 27.1 | 26.9 |
| Slump (Spread), inches | 5 | (24) | (27) | 5¼ |

The number of days required to achieve a water vapor emission rate of 3 lb/1000 ft²·24 hr for the cementitious mixes shown in Table 10 were obtained by casting each of the samples in a 2 foot×2 foot×5½ inch deep panel lined with polyethylene. The plates, not subjected to a sealed cure time, were allowed to dry at 50% relative humidity and 73° F. in a drying room. The water vapor emissions data were obtained by using the calcium chloride dome tests according to the ASTM F1869 test standard. The results are shown in Table 11.

TABLE 11

|  | Sample 14 | Sample 15 | Sample 16 | Sample 17 |
|---|---|---|---|---|
| Drying Time needed for 3 lb/1000 ft² · 24 hr Emissions, days | >53 | 36 | 36 | >53 |

As this data shows, the addition of a finely divided calcium carbonate enables the amount of excess water to be further reduced.

Example 7

The purpose of the tests in EX. 7 were to demonstrate the effect of partial substitution with a finely divided material (finely divided ground granulated blast furnace slag and finely divided type F fly ash) generally smaller than a U.S. standard sieve size 200 or particles having a size less than about 75 microns along with a superplasticizer in the cementitious compositions using the sample mixes of Table 12.

TABLE 12

| Compound/Property | Sample 18 | Sample 19 | Sample 20 | Sample 21 | Sample 22 |
|---|---|---|---|---|---|
| Cement, lb | 800 | 600 | 400 | 560 | 680 |
| Ground Slag, lb | — | 200 | 400 | — | — |
| Fly Ash - Type F, lb | — | — | — | 240 | 120 |
| Sand, lb | 1,300 | 1,300 | 1,300 | 1,300 | 1,300 |
| GLENIUM 3000, oz/100 lb cement | 8 | 8 | 8 | 8 | 8 |
| Water, lb | 195 | 190 | 190 | 210 | 198 |
| water to cement ratio | 0.24 | 0.24 | 0.24 | 0.26 | 0.25 |
| Density, lb/ft³ (pcf) | 151 | 150 | 149 | 144 | 148 |
| Yield, cc³ | 950 | 957 | 960 | 1006 | 971 |
| Slump (Spread), inches | flowing | flowing | flowing | flowing | flowing |

The sample mixes were analyzed using the mortar method, as further disclosed herein. Mortar of the same workability level as the concrete of the investigation was mixed and cast in 6 inch×6 inch plastic pans to a depth of 1⅝ inches. The samples were cured unsealed for 24 hours and then sealed for a 14-day cure. Vapor loss measurements were determined based on the changes in weight of the samples and is reported in Table 13.

TABLE 13

|  | Sample 18 | Sample 19 | Sample 20 | Sample 21 | Sample 22 |
|---|---|---|---|---|---|
| Total Water Vapor Loss, gr | 3.7 | 2.9 | 4.4 | 7.4 | 5.6 |

Increasing the amount of ground granulated blast furnace slag, as shown in samples 19 and 20, resulted in the same water to cementitious ratio and produced a vapor loss in the same range as sample 18, the control mix. Substitution of type F fly ash in samples 21 and 22 resulted in progressively higher vapor emissions over the curing period, but represent rates that still are within a satisfactory range.

Example 8

The sample mixes of Table 14 were used to generate a correlation between the water losses measured from the 6 inch×6 inch mortar samples pans and the water vapor emissions using the 2 foot×2 foot concrete panels.

TABLE 14

|  | Sample 23 | Sample 24 | Sample 25 | Sample 26 | Sample 27 | Sample 28 |
|---|---|---|---|---|---|---|
| Portland Cement, gr | 520 | 520 | 520 | 520 | 650 | 650 |
| Sand, gr | 1,540.00 | 1,540 | 1,540 | 1,540 | 1,430 | 1,430 |
| Glenium 3000, oz/100 lb cement | 0 | 4 | 8 | 16 | 0 | 4 |
| Water, gr | 285 | 268 | 228 | 205 | 289 | 238 |
| water to cement ratio | 0.55 | 0.52 | 0.44 | 0.39 | 0.44 | 0.37 |
| Density, lb/ft³ (pcf) | 138 | 139 | 145 | 146 | 141 | 144 |
| Yield, cc³ | 1057 | 1046 | 988 | 971 | 1030 | 1006 |
| Slump, inches | 5 | 5¼ | flowing | flowing | 5 | flowing |
| Vapor Loss, gr | 29.7 | 23.4 | 11.8 | 9.9 | 17.3 | 9.7 |

|  | Sample 29 | Sample 30 | Sample 31 | Sample 32 | Sample 33 | Sample 34 |
|---|---|---|---|---|---|---|
| Portland Cement, gr | 650 | 650 | 780 | 780 | 780 | 780 |
| Sand, gr | 1,430 | 1,430 | 1,315 | 1,315 | 1,315 | 1,315 |
| Glenium 3000, oz/100 lb cement | 8 | 16 | 0 | 4 | 8 | 16 |
| Water, gr | 220 | 195 | 300 | 282 | 218 | 187 |
| water to cement ratio | 0.34 | 0.30 | 0.38 | 0.36 | 0.28 | 0.24 |
| Density, lb/ft³ (pcf) | 146 | 149 | 142 | 144 | 148 | 142 |
| Yield, cc³ | 984 | 955 | 1050 | 991 | 978 | 942 |
| Slump, inches | flowing | flowing | 4¾ | 4½ | flowing | flowing |
| Vapor Loss, gr | 6.3 | 4.6 | 13.6 | 8.2 | 4.1 | 2.6 |

FIG. 2 is a graphical illustration of the water loss from the mortar pans versus the water vapor emissions measured from the concrete panels.

Example 9

The sample mixes of Table 15 were used to analyze the variations in water loss measured from the 6 inch×6 inch mortar samples pans for mixes comprising cements and sands from five different regions.

TABLE 15

|  | Sample 35 | Sample 36 | Sample 37 | Sample 38 | Sample 39 | Sample 40 | Sample 41 | Sample 42 | Sample 43 |
|---|---|---|---|---|---|---|---|---|---|
| Cement, gr |  |  |  |  |  |  |  |  |  |
| Permanente, CA | 650 | — | — | — | — | — | — | — | — |
| Maryland | — | 650 | — | — | — | 650 | — | — | — |
| Texas | — | — | 650 | — | — | — | 650 | — | — |
| Michigan | — | — | — | 650 | — | — | — | 650 | — |
| Tennessee | — | — | — | — | 650 | — | — | — | 650 |
| Sand, gr |  |  |  |  |  |  |  |  |  |
| Seacheldt | 1,430 | 1,430 | 1,430 | 1,430 | 1,430 | — | — | — | — |
| Maryland | — | — | — | — | — | 1,430 | — | — | — |
| Texas | — | — | — | — | — | — | 1,430 | — | — |

TABLE 15-continued

|  | Sample 35 | Sample 36 | Sample 37 | Sample 38 | Sample 39 | Sample 40 | Sample 41 | Sample 42 | Sample 43 |
|---|---|---|---|---|---|---|---|---|---|
| Michigan | — | — | — | — | — | — | — | 1,430 | — |
| Tennessee | — | — | — | — | — | — | — | — | 1,430 |
| Glenium 3000, oz/100 lb cement | 16 | 16 | 16 | 16 | 16 | 35 | 16 | 16 | 16 |
| Water, gr | 190 | 208 | 208 | 216 | 210 | 224 | 204 | 216 | 206 |
| water to cement ratio | 0.29 | 0.32 | 0.32 | 0.33 | 0.32 | 0.34 | 0.32 | 0.33 | 0.32 |
| Density, lb/ft$^3$ (pcf) | 149 | 148 | 148 | 146 | 147 | 144 | 148 | 146 | 149 |
| Yield, cc$^3$ | 953 | 968 | 967 | 985 | 976 | 1003 | 970 | 988 | 960 |
| Slump, inches | 8.0 | 6.3 | 6.0 | 5.5 | 5.5 | 5.0 | 8.0 | 5.5 | 7.3 |
| Mix Temperature, °F. | 75.0 | 76.0 | 75.0 | 76.0 | 75.0 | 75.0 | 76.0 | 75.0 | 75.0 |
| Vapor Loss, gr | 8.0 | 6.3 | 6.0 | 5.5 | 5.5 | 5.0 | 8.0 | 5.5 | 7.3 |

The average vapor loss for these samples was 6.34, while the standard deviation for the sample was 1.08.

All publications mentioned herein, including patents, patent applications, and journal articles are incorporated herein by reference in their entireties including the references cited therein, which are also incorporated herein by reference. The publications discussed herein are provided solely for their disclosure prior to the filing date of the present application. Nothing herein is to be construed as an admission that the present invention is not entitled to antedate such publication by virtue of prior invention. Neither should the citation of documents herein be construed as an admission that the cited documents are considered material to the patentability of the claims of the various embodiments of the invention. Further, the dates of publication provided may be different from the actual publication dates which may need to be independently confirmed.

Many modifications and other embodiments of the invention set forth herein will come to mind to one skilled in the art to which this invention pertains having the benefit of the teachings presented in the descriptions herein and the associated drawings. For example, though various methods are disclosed herein, one skilled in the art will appreciate that various other methods now know or conceived in the art will be applied to a subject in conjunction with the methods of treatments or therapies disclosed herein. Therefore, it is to be understood that the invention is not to be limited to the specific embodiments disclosed and that modifications and other embodiments are intended to be included within the scope of the appended claims.

That which is claimed:

1. A method for estimating a property of a concrete comprising the steps of:
    preparing a mortar mixture that comprises compounds of a cementitious mix used to prepare the concrete except that the mortar mixture is substantially free of any coarse aggregate;
    casting the mortar mixture into a sample;
    equilibrating the sample to a selected set of conditions;
    calculating a daily weight loss of the sample; and
    estimating the property of the concrete using an established correlation based on the daily weight loss.

2. The method according to claim 1, wherein the property is selected from the group consisting of a water vapor emission, an internal relative humidity, a required water content, a water to cementitious ratio, and any combination thereof.

3. The method according to claim 2, wherein the step of curing the sample comprises the steps of:
    sealing the sample to prevent any further vapor loss; and
    curing the sample for a period of time.

4. The method according to claim 3, wherein the step of curing the sample additionally comprises the step of delaying sealing the sample for a specified period of time.

5. The method according to claim 4, wherein the compounds of the mortar mixture are proportioned substantially the same as the compounds of the cementitious mix.

6. The method according to claim 1, additionally comprising the step of curing the sample before the equilibrating step.

7. The method according to claim 1, wherein the procedure for preparing the mortar mixture comprises the steps of
    combining a sufficient amount of water with an admix to form a paste mixture;
    adding a sand to the paste mixture to form a mortar mixture;
    mixing the mortar mixture; and
    continuing to add any additional water as the mortar mixture continues to be mixed to achieve a desired workability.

8. The method according to claim 1, wherein the sample has a surface to volume ratio of from about 0.6 in$^{-1}$ to about 0.8 in$^{-1}$.

9. The method according to claim 1, wherein the sample has a depth of about 1⅜ inches.

* * * * *